US010143517B2

(12) United States Patent
Ransbury et al.

(10) Patent No.: US 10,143,517 B2
(45) Date of Patent: Dec. 4, 2018

(54) SYSTEMS AND METHODS FOR ASSESSMENT OF CONTACT QUALITY

(71) Applicant: LuxCath, LLC, Boston, MA (US)

(72) Inventors: Terrance J. Ransbury, Chapel Hill, NC (US); Kenneth C. Armstrong, Cary, NC (US); Omar Amirana, Cambridge, MA (US); Cinnamon Larson, Carrboro, NC (US); James Bowen, Belmont, NC (US)

(73) Assignee: LuxCath, LLC, Boston, MA (US)

( * ) Notice: Subject to any disclaimer, the term of this patent is extended or adjusted under 35 U.S.C. 154(b) by 437 days.

(21) Appl. No.: 14/931,325

(22) Filed: Nov. 3, 2015

(65) Prior Publication Data

US 2016/0120602 A1 May 5, 2016

Related U.S. Application Data

(60) Provisional application No. 62/074,615, filed on Nov. 3, 2014.

(51) Int. Cl.
*A61B 18/14* (2006.01)
*A61B 18/18* (2006.01)
(Continued)

(52) U.S. Cl.
CPC .......... *A61B 18/1492* (2013.01); *A61B 18/18* (2013.01); *A61B 18/22* (2013.01);
(Continued)

(58) Field of Classification Search
CPC ..... A61B 28/1492; A61B 28/18; A61B 28/22; A61B 28/082; A61B 2018/00577;
(Continued)

(56) References Cited

U.S. PATENT DOCUMENTS 5,074,306 A 12/1991 Green et al.
5,187,572 A 2/1993 Nakamura et al.
(Continued)

FOREIGN PATENT DOCUMENTS

CN 1289239 3/2001
CN 1764419 4/2006
(Continued)

OTHER PUBLICATIONS

Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).
(Continued)

*Primary Examiner* — Michael Peffley
(74) *Attorney, Agent, or Firm* — Greenberg Traurig, LLP; David J. Dykeman; Roman Fayerberg

(57) ABSTRACT

Ablation and visualization systems and methods to access quality of contact between a catheter and tissue are provided. In some embodiments, a method for monitoring tissue ablation of the present disclosure comprises advancing a distal tip of an ablation catheter to a tissue in need of ablation; illuminating the tissue with UV light to excite NADH in the tissue, wherein the tissue is illuminated in a radial direction, an axial direction, or both; determining from a level of NADH fluorescence in the illuminated tissue when the distal tip of the catheter is in contact with the tissue; and delivering ablation energy to the tissue to form a lesion in the tissue.

33 Claims, 10 Drawing Sheets

(51) Int. Cl.
*A61B 18/22* (2006.01)
*A61B 17/00* (2006.01)
*A61B 18/00* (2006.01)
*A61B 18/02* (2006.01)
*A61B 90/00* (2016.01)

(52) U.S. Cl.
CPC .............. *A61B 2017/00057* (2013.01); *A61B 2018/00577* (2013.01); *A61B 2018/0212* (2013.01); *A61B 2090/065* (2016.02); *A61B 2090/3784* (2016.02); *A61B 2218/002* (2013.01)

(58) Field of Classification Search
CPC .. A61B 2018/0212; A61B 2018/00351; A61B 2018/00904; A61B 2018/00357; A61B 2018/20359; A61B 2018/2261; A61B 2018/00363; A61B 2018/00375
See application file for complete search history.

(56) References Cited

U.S. PATENT DOCUMENTS

| | | | |
|---|---|---|---|
| 5,350,375 A * | 9/1994 | Deckelbaum | A61B 18/245 128/898 |
| 5,419,323 A | 5/1995 | Kittrell et al. | |
| 5,421,337 A | 6/1995 | Richards-Kortum et al. | |
| 5,507,287 A | 4/1996 | Palcic et al. | |
| 5,590,660 A | 1/1997 | MacAulay et al. | |
| 5,657,760 A | 8/1997 | Ying et al. | |
| 5,713,364 A | 2/1998 | DeBaryshe et al. | |
| 5,749,830 A | 5/1998 | Kaneko et al. | |
| 5,833,688 A | 11/1998 | Sieben et al. | |
| 5,904,651 A | 5/1999 | Swanson et al. | |
| 5,954,665 A | 9/1999 | Ben Haim | |
| 6,064,069 A | 5/2000 | Nakano et al. | |
| 6,112,123 A | 8/2000 | Kelleher et al. | |
| 6,124,597 A | 9/2000 | Shehada et al. | |
| 6,174,291 B1 | 1/2001 | McMahon et al. | |
| 6,178,346 B1 | 1/2001 | Amundson et al. | |
| 6,197,021 B1 | 3/2001 | Panescu et al. | |
| 6,217,573 B1 | 4/2001 | Webster et al. | |
| 6,219,566 B1 | 4/2001 | Weersink et al. | |
| 6,251,107 B1 | 6/2001 | Schaer | |
| 6,289,236 B1 | 9/2001 | Koenig et al. | |
| 6,309,352 B1 | 10/2001 | Oraevsky et al. | |
| 6,343,228 B1 | 1/2002 | Qu | |
| 6,423,055 B1 | 7/2002 | Farr et al. | |
| 6,423,057 B1 | 7/2002 | He et al. | |
| 6,450,971 B1 | 9/2002 | Andrus et al. | |
| 6,516,217 B1 | 2/2003 | Tsujita | |
| 6,522,913 B2 | 2/2003 | Swanson et al. | |
| 6,542,767 B1 | 4/2003 | McNichols et al. | |
| 6,572,609 B1 | 6/2003 | Farr et al. | |
| 6,584,360 B2 | 6/2003 | Francischelli et al. | |
| 6,626,900 B1 | 9/2003 | Sinofsky et al. | |
| 6,648,883 B2 | 11/2003 | Francischelli et al. | |
| 6,658,279 B2 | 12/2003 | Swanson et al. | |
| 6,663,622 B1 | 12/2003 | Foley et al. | |
| 6,663,627 B2 | 12/2003 | Francischelli et al. | |
| 6,671,535 B1 | 12/2003 | McNichols et al. | |
| 6,697,657 B1 | 2/2004 | Shehada et al. | |
| 6,706,038 B2 | 3/2004 | Francischelli et al. | |
| 6,716,196 B2 | 4/2004 | Lesh et al. | |
| 6,743,225 B2 | 6/2004 | Sanchez et al. | |
| 6,746,401 B2 | 6/2004 | Panescu | |
| 6,761,716 B2 | 7/2004 | Kadhiresan et al. | |
| 6,825,928 B2 | 11/2004 | Liu et al. | |
| 6,936,047 B2 | 8/2005 | Nasab et al. | |
| 6,937,885 B1 | 8/2005 | Lewis et al. | |
| 6,942,657 B2 | 9/2005 | Sinofsky et al. | |
| 6,953,457 B2 | 10/2005 | Farr et al. | |
| 6,974,454 B2 | 12/2005 | Hooven | |
| 6,975,898 B2 | 12/2005 | Seibel | |
| 6,979,290 B2 | 12/2005 | Mourlas et al. | |
| 6,989,010 B2 | 1/2006 | Francischelli et al. | |
| 7,001,383 B2 | 2/2006 | Keidar | |
| 7,029,470 B2 | 4/2006 | Francischelli et al. | |
| 7,047,068 B2 | 5/2006 | Haissaguerre | |
| 7,130,672 B2 | 10/2006 | Pewzner et al. | |
| 7,192,427 B2 | 3/2007 | Chapelon et al. | |
| 7,207,984 B2 | 4/2007 | Fan et al. | |
| 7,232,437 B2 | 6/2007 | Berman et al. | |
| 7,235,045 B2 | 6/2007 | Wang et al. | |
| 7,250,048 B2 | 7/2007 | Francischelli et al. | |
| 7,252,664 B2 | 8/2007 | Nasab et al. | |
| 7,255,695 B2 | 8/2007 | Falwell et al. | |
| 7,289,205 B2 | 10/2007 | Yaroslaysky et al. | |
| 7,306,593 B2 | 12/2007 | Keidar et al. | |
| 7,338,485 B2 | 3/2008 | Brucker et al. | |
| 7,357,796 B2 | 4/2008 | Farr et al. | |
| 7,367,944 B2 | 5/2008 | Rosemberg et al. | |
| 7,367,972 B2 | 5/2008 | Francischelli et al. | |
| 7,497,858 B2 | 3/2009 | Chapelon et al. | |
| 7,527,625 B2 | 5/2009 | Knight et al. | |
| 7,534,204 B2 | 5/2009 | Starksen et al. | |
| 7,539,530 B2 | 5/2009 | Caplan et al. | |
| 7,587,236 B2 | 9/2009 | Demos et al. | |
| 7,591,816 B2 | 9/2009 | Wang et al. | |
| 7,596,404 B2 | 9/2009 | Maier et al. | |
| 7,598,088 B2 | 10/2009 | Balas | |
| 7,640,046 B2 | 12/2009 | Pastore | |
| 7,662,152 B2 | 2/2010 | Sharareh et al. | |
| 7,681,579 B2 | 3/2010 | Schwartz | |
| 7,727,229 B2 | 6/2010 | He et al. | |
| 7,727,231 B2 | 6/2010 | Swanson | |
| 7,729,750 B2 | 6/2010 | Tromberg et al. | |
| 7,766,907 B2 | 8/2010 | Dando et al. | |
| 7,776,033 B2 | 8/2010 | Swanson | |
| 7,822,460 B2 | 10/2010 | Halperin et al. | |
| 7,824,397 B2 | 11/2010 | McAuley | |
| 7,824,399 B2 | 11/2010 | Francischelli et al. | |
| 7,837,676 B2 | 11/2010 | Sinelnikov et al. | |
| 7,846,157 B2 | 12/2010 | Kozel | |
| 7,862,561 B2 | 1/2011 | Swanson et al. | |
| 7,877,128 B2 | 1/2011 | Schwartz | |
| 7,918,850 B2 | 4/2011 | Govari et al. | |
| 7,930,016 B1 | 4/2011 | Saadat | |
| 7,942,871 B2 | 5/2011 | Thapliyal et al. | |
| 7,950,397 B2 | 5/2011 | Thapliyal et al. | |
| 7,974,683 B2 | 7/2011 | Balas et al. | |
| 7,976,537 B2 | 7/2011 | Lieber et al. | |
| 7,979,107 B2 | 7/2011 | Lin et al. | |
| 7,996,078 B2 | 8/2011 | Paul et al. | |
| 8,007,433 B2 | 8/2011 | Iketani | |
| 8,024,027 B2 | 9/2011 | Freeman et al. | |
| 8,025,661 B2 | 9/2011 | Arnold et al. | |
| 8,050,746 B2 | 11/2011 | Saadat et al. | |
| 8,078,266 B2 | 12/2011 | Saadat et al. | |
| 8,123,742 B2 | 2/2012 | Berger | |
| 8,123,745 B2 | 2/2012 | Beeckler et al. | |
| 8,129,105 B2 | 3/2012 | Zuckerman | |
| 8,131,350 B2 | 3/2012 | Saadat et al. | |
| 8,137,333 B2 | 3/2012 | Saadat et al. | |
| 8,146,603 B2 | 4/2012 | Thapliyal et al. | |
| 8,147,484 B2 | 4/2012 | Lieber et al. | |
| 8,152,795 B2 | 4/2012 | Farr et al. | |
| 8,160,680 B2 | 4/2012 | Boyden et al. | |
| 8,175,688 B2 | 5/2012 | Lewis et al. | |
| 8,180,436 B2 | 5/2012 | Boyden et al. | |
| 8,188,446 B2 | 5/2012 | Ohno | |
| 8,195,271 B2 | 6/2012 | Rahn | |
| 8,203,709 B2 | 6/2012 | Ishii | |
| 8,219,183 B2 | 7/2012 | Mashke et al. | |
| 8,221,310 B2 | 7/2012 | Saadat et al. | |
| 8,235,985 B2 | 8/2012 | Saadat et al. | |
| 8,241,272 B2 | 8/2012 | Arnold et al. | |
| 8,267,926 B2 | 9/2012 | Paul et al. | |
| 8,277,444 B2 | 10/2012 | Arnold et al. | |
| 8,298,227 B2 | 10/2012 | Leo et al. | |
| 8,309,346 B2 | 11/2012 | Zuckerman | |
| 8,317,783 B2 | 11/2012 | Cao et al. | |
| 8,333,012 B2 | 12/2012 | Rothe et al. | |
| 8,353,907 B2 | 1/2013 | Winkler et al. | |

(56) References Cited

U.S. PATENT DOCUMENTS

| | | |
|---|---|---|
| 8,357,149 B2 | 1/2013 | Govari et al. |
| 8,366,705 B2 | 2/2013 | Arnold et al. |
| 8,369,922 B2 | 2/2013 | Paul et al. |
| 8,382,750 B2 | 2/2013 | Brannan |
| 8,403,925 B2 | 3/2013 | Miller et al. |
| 8,414,508 B2 | 4/2013 | Thapliyal et al. |
| 8,417,321 B2 | 4/2013 | Saadat et al. |
| 8,417,323 B2 | 4/2013 | Uzunbajakava et al. |
| 8,419,613 B2 | 4/2013 | Saadat et al. |
| 8,435,232 B2 | 5/2013 | Aeby et al. |
| 8,444,639 B2 | 5/2013 | Arnold et al. |
| 8,460,285 B2 | 6/2013 | Wang et al. |
| 8,463,366 B2 | 6/2013 | Freeman et al. |
| 8,500,730 B2 | 8/2013 | Lee et al. |
| 8,504,132 B2 | 8/2013 | Friedman et al. |
| 8,511,317 B2 | 8/2013 | Thapliyal et al. |
| 8,540,704 B2 | 9/2013 | Melsky et al. |
| 8,548,567 B2 | 10/2013 | Maschke et al. |
| 8,556,892 B2 | 10/2013 | Hong et al. |
| 8,583,220 B2 | 11/2013 | Schwartz |
| 8,603,084 B2 | 12/2013 | Fish et al. |
| 8,607,800 B2 | 12/2013 | Thapliyal et al. |
| 8,628,520 B2 | 1/2014 | Sharareh et al. |
| 8,641,705 B2 | 2/2014 | Leo et al. |
| 8,641,706 B2 | 2/2014 | Lieber et al. |
| 8,690,758 B2 | 4/2014 | Matsumoto |
| 8,702,690 B2 | 4/2014 | Paul et al. |
| 8,709,008 B2 | 4/2014 | Willis et al. |
| 8,728,077 B2 | 5/2014 | Paul et al. |
| 8,755,860 B2 | 6/2014 | Paul et al. |
| 8,774,906 B2 | 7/2014 | Harks et al. |
| 8,808,281 B2 | 8/2014 | Emmons et al. |
| 8,849,380 B2 | 9/2014 | Patwardhan |
| 8,858,495 B2 | 10/2014 | Tegg et al. |
| 8,876,817 B2 | 11/2014 | Avitall et al. |
| 8,894,589 B2 | 11/2014 | Leo et al. |
| 8,894,641 B2 | 11/2014 | Brannan |
| 8,900,219 B2 | 12/2014 | Sinofsky et al. |
| 8,900,225 B2 | 12/2014 | Bar-Tal et al. |
| 8,900,228 B2 | 12/2014 | Grunewald et al. |
| 8,900,229 B2 | 12/2014 | Govari et al. |
| 8,906,011 B2 | 12/2014 | Gelbart et al. |
| 8,915,878 B2 | 12/2014 | Winkler et al. |
| 8,923,959 B2 | 12/2014 | Boveja et al. |
| 8,926,604 B2 | 1/2015 | Govari et al. |
| 8,948,851 B2 | 2/2015 | Leblond et al. |
| 8,951,247 B2 | 2/2015 | Ding et al. |
| 8,986,292 B2 | 3/2015 | Sliwa et al. |
| 8,986,298 B2 | 3/2015 | Lee et al. |
| 8,998,890 B2 | 4/2015 | Paul et al. |
| 8,998,892 B2 | 4/2015 | Winkler et al. |
| 8,998,893 B2 | 4/2015 | Avitall |
| 9,008,746 B2 | 4/2015 | Pastore et al. |
| 9,014,789 B2 | 4/2015 | Mercader et al. |
| 9,084,611 B2 | 7/2015 | Amirana et al. |
| 2002/0042556 A1 | 4/2002 | Sugimoto et al. |
| 2002/0123666 A1 | 9/2002 | Matsumoto |
| 2002/0143326 A1 | 10/2002 | Foley et al. |
| 2003/0028188 A1 | 2/2003 | Paddock et al. |
| 2003/0120142 A1 | 6/2003 | Dubuc et al. |
| 2003/0120144 A1 | 6/2003 | Grabek et al. |
| 2003/0208252 A1 | 11/2003 | O' Boyle et al. |
| 2004/0073206 A1 | 4/2004 | Foley et al. |
| 2004/0092806 A1 | 5/2004 | Sagon et al. |
| 2004/0097788 A1 | 5/2004 | Mourlas et al. |
| 2004/0138656 A1 | 7/2004 | Francischelli et al. |
| 2004/0187875 A1 | 9/2004 | He et al. |
| 2004/0267326 A1 | 12/2004 | Ocel et al. |
| 2005/0014995 A1 | 1/2005 | Amundson et al. |
| 2005/0043637 A1 | 2/2005 | Caplan et al. |
| 2005/0075629 A1 | 4/2005 | Chapelon et al. |
| 2005/0119523 A1 | 6/2005 | Starksen et al. |
| 2005/0197623 A1 | 9/2005 | Leeflang et al. |
| 2005/0215899 A1 | 9/2005 | Trahey et al. |
| 2005/0228452 A1 | 10/2005 | Mourlas et al. |
| 2005/0251125 A1 | 11/2005 | Pless et al. |
| 2005/0283195 A1 | 12/2005 | Pastore et al. |
| 2006/0013454 A1 | 1/2006 | Flewelling et al. |
| 2006/0089636 A1 | 4/2006 | Christopherson et al. |
| 2006/0122587 A1 | 6/2006 | Sharareh |
| 2006/0184048 A1 | 8/2006 | Saadat |
| 2006/0229515 A1 | 10/2006 | Sharareh et al. |
| 2007/0015964 A1 | 1/2007 | Eversull et al. |
| 2007/0016130 A1 | 1/2007 | Leeflang et al. |
| 2007/0038126 A1 | 2/2007 | Pyle et al. |
| 2007/0049827 A1 | 3/2007 | Donaldson et al. |
| 2007/0083217 A1 | 4/2007 | Eversull et al. |
| 2007/0167828 A1 | 7/2007 | Saadat |
| 2007/0185479 A1 | 8/2007 | Lau |
| 2007/0225697 A1 | 9/2007 | Shroff et al. |
| 2007/0270789 A1 | 11/2007 | Berger |
| 2007/0270792 A1 | 11/2007 | Hennemann et al. |
| 2007/0270795 A1 | 11/2007 | Francischelli et al. |
| 2007/0276259 A1 | 11/2007 | Okawa et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0015569 A1 | 1/2008 | Saadat et al. |
| 2008/0033241 A1 | 2/2008 | Peh et al. |
| 2008/0058650 A1 | 3/2008 | Saadat et al. |
| 2008/0058785 A1* | 3/2008 | Boyden ............... A61B 5/0071 606/13 |
| 2008/0097476 A1 | 4/2008 | Peh et al. |
| 2008/0101677 A1 | 5/2008 | Mashke et al. |
| 2008/0119694 A1 | 5/2008 | Lee |
| 2008/0154257 A1 | 6/2008 | Sharareh et al. |
| 2008/0172049 A1 | 7/2008 | Bredno et al. |
| 2008/0183036 A1 | 7/2008 | Saadat et al. |
| 2008/0214889 A1 | 9/2008 | Saadat et al. |
| 2008/0221448 A1 | 9/2008 | Khuri-Yakub et al. |
| 2008/0228032 A1 | 9/2008 | Starksen et al. |
| 2008/0228079 A1 | 9/2008 | Donaldson et al. |
| 2008/0243214 A1 | 10/2008 | Koblish |
| 2008/0275300 A1 | 11/2008 | Rothe et al. |
| 2008/0281293 A1 | 11/2008 | Peh et al. |
| 2008/0300589 A1 | 12/2008 | Paul et al. |
| 2009/0012367 A1 | 1/2009 | Chin et al. |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076373 A1 | 3/2009 | Maschke |
| 2009/0076375 A1 | 3/2009 | Maschke |
| 2009/0082623 A1 | 3/2009 | Rothe et al. |
| 2009/0082660 A1 | 3/2009 | Rahn et al. |
| 2009/0125022 A1 | 5/2009 | Saadat et al. |
| 2009/0131931 A1 | 5/2009 | Lee et al. |
| 2009/0143640 A1 | 6/2009 | Saadat et al. |
| 2009/0203962 A1 | 8/2009 | Miller et al. |
| 2009/0221871 A1 | 9/2009 | Peh et al. |
| 2009/0227999 A1 | 9/2009 | Willis et al. |
| 2009/0253991 A1 | 10/2009 | Balas et al. |
| 2009/0275799 A1 | 11/2009 | Saadat et al. |
| 2009/0281541 A1 | 11/2009 | Ibrahim et al. |
| 2009/0299354 A1 | 12/2009 | Melsky et al. |
| 2009/0299363 A1 | 12/2009 | Saadat et al. |
| 2009/0306643 A1 | 12/2009 | Pappone et al. |
| 2010/0041986 A1 | 2/2010 | Nguyen et al. |
| 2010/0081127 A1 | 4/2010 | Maier et al. |
| 2010/0081948 A1 | 4/2010 | Pastore et al. |
| 2010/0084563 A1 | 4/2010 | Ohno |
| 2010/0114094 A1 | 5/2010 | Thapliyal et al. |
| 2010/0130836 A1 | 5/2010 | Malchano et al. |
| 2010/0152728 A1 | 6/2010 | Park et al. |
| 2010/0198065 A1 | 8/2010 | Thapliyal et al. |
| 2010/0204544 A1 | 8/2010 | Takei |
| 2010/0204561 A1 | 8/2010 | Saadat |
| 2010/0228247 A1 | 9/2010 | Paul et al. |
| 2010/0241117 A1 | 9/2010 | Paul et al. |
| 2010/0312094 A1 | 12/2010 | Guttman et al. |
| 2010/0312096 A1 | 12/2010 | Guttman et al. |
| 2010/0331838 A1 | 12/2010 | Ibrahim et al. |
| 2011/0019893 A1 | 1/2011 | Rahn et al. |
| 2011/0029058 A1 | 2/2011 | Swanson |

(56) References Cited

U.S. PATENT DOCUMENTS

| | | |
|---|---|---|
| 2011/0042580 A1 | 2/2011 | Wilson et al. |
| 2011/0066147 A1 | 3/2011 | He et al. |
| 2011/0082450 A1 | 4/2011 | Melsky et al. |
| 2011/0082451 A1 | 4/2011 | Melsky et al. |
| 2011/0082452 A1 | 4/2011 | Melsky et al. |
| 2011/0117025 A1 | 5/2011 | Dacosta et al. |
| 2011/0144524 A1 | 6/2011 | Fish et al. |
| 2011/0230903 A1 | 9/2011 | Bertolero |
| 2011/0275932 A1 | 11/2011 | Leblond et al. |
| 2011/0276046 A1 | 11/2011 | Heimbecher et al. |
| 2011/0282250 A1 | 11/2011 | Fung et al. |
| 2011/0313417 A1 | 12/2011 | De La Rama et al. |
| 2012/0029504 A1 | 2/2012 | Afonso et al. |
| 2012/0123276 A1 | 5/2012 | Govari et al. |
| 2012/0143177 A1 | 6/2012 | Avitall |
| 2012/0150046 A1 | 6/2012 | Watson et al. |
| 2012/0184812 A1 | 7/2012 | Terakawa |
| 2012/0184813 A1 | 7/2012 | Terakawa |
| 2012/0197243 A1 | 8/2012 | Sherman et al. |
| 2012/0215112 A1 | 8/2012 | Lewis et al. |
| 2012/0323237 A1 | 12/2012 | Paul et al. |
| 2012/0326055 A1 | 12/2012 | Wilson et al. |
| 2013/0006116 A1 | 1/2013 | Kim et al. |
| 2013/0079645 A1* | 3/2013 | Amirana ............ A61B 90/35 600/479 |
| 2013/0085416 A1 | 4/2013 | Mest |
| 2013/0096593 A1 | 4/2013 | Thapliyal et al. |
| 2013/0096594 A1 | 4/2013 | Thapliyal et al. |
| 2013/0102862 A1 | 4/2013 | Amirana et al. |
| 2013/0107002 A1 | 5/2013 | Kikuchi |
| 2013/0137949 A1 | 5/2013 | Freeman et al. |
| 2013/0150693 A1 | 6/2013 | D'Angelo et al. |
| 2013/0150732 A1 | 6/2013 | Manzke et al. |
| 2013/0158545 A1 | 6/2013 | Govari et al. |
| 2013/0172742 A1 | 7/2013 | Rankin et al. |
| 2013/0172875 A1 | 7/2013 | Govari et al. |
| 2013/0226163 A1 | 8/2013 | Peled et al. |
| 2013/0237841 A1 | 9/2013 | Freeman et al. |
| 2013/0253330 A1 | 9/2013 | Demos |
| 2013/0261455 A1 | 10/2013 | Thapliyal et al. |
| 2013/0267875 A1 | 10/2013 | Thapliyal et al. |
| 2013/0282005 A1 | 10/2013 | Koch et al. |
| 2013/0289358 A1 | 10/2013 | Melsky et al. |
| 2013/0296840 A1 | 11/2013 | Condie et al. |
| 2013/0310680 A1 | 11/2013 | Werahera et al. |
| 2013/0331831 A1 | 12/2013 | Werneth et al. |
| 2014/0031802 A1 | 1/2014 | Melsky |
| 2014/0058244 A1 | 2/2014 | Krocak |
| 2014/0058246 A1 | 2/2014 | Boveja et al. |
| 2014/0081253 A1 | 3/2014 | Kumar et al. |
| 2014/0088418 A1 | 3/2014 | Radulescu et al. |
| 2014/0107430 A1 | 4/2014 | Deno et al. |
| 2014/0121537 A1 | 5/2014 | Aeby et al. |
| 2014/0121660 A1 | 5/2014 | Hauck |
| 2014/0148703 A1 | 5/2014 | Deladi et al. |
| 2014/0163360 A1 | 6/2014 | Stevens-Wright et al. |
| 2014/0163543 A1 | 6/2014 | Allison et al. |
| 2014/0171806 A1 | 6/2014 | Govari et al. |
| 2014/0171936 A1 | 6/2014 | Govari et al. |
| 2014/0180273 A1 | 6/2014 | Nair |
| 2014/0194867 A1 | 7/2014 | Fish et al. |
| 2014/0194869 A1 | 7/2014 | Leo et al. |
| 2014/0275972 A1 | 9/2014 | George et al. |
| 2014/0276687 A1 | 9/2014 | Goodman et al. |
| 2014/0276771 A1 | 9/2014 | Miller et al. |
| 2014/0316280 A1* | 10/2014 | Mueller ............ A61B 5/0071 600/476 |
| 2014/0324085 A1 | 10/2014 | Thapliyal et al. |
| 2014/0350547 A1 | 11/2014 | Sharareh et al. |
| 2015/0038824 A1 | 2/2015 | Lupotti |
| 2015/0073245 A1 | 3/2015 | Klimovitch et al. |
| 2015/0099979 A1 | 4/2015 | Caves et al. |
| 2015/0141847 A1 | 5/2015 | Sarvazyan |
| 2015/0164332 A1 | 6/2015 | Mercader et al. |
| 2015/0196202 A1 | 7/2015 | Mercader et al. |
| 2015/0327753 A1 | 11/2015 | Amirana et al. |
| 2015/0346100 A1 | 12/2015 | Racowsky et al. |
| 2016/0120599 A1 | 5/2016 | Amirana et al. |
| 2016/0120602 A1 | 5/2016 | Ransbury et al. |
| 2016/0143522 A1 | 5/2016 | Ransbury et al. |
| 2017/0014202 A1 | 1/2017 | Ransbury et al. |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 106028914 | 10/2016 |
| DE | 102005021205 | 11/2006 |
| DE | 102011083522 | 3/2013 |
| EP | 2691041 | 2/2014 |
| JP | 60182928 A | 9/1985 |
| JP | 63-262613 | 10/1988 |
| JP | 10150177 A | 6/1998 |
| JP | 2006158546 A | 6/2006 |
| NL | 2002010 | 10/2009 |
| WO | WO 1997/037622 | 10/1997 |
| WO | 2001001854 | 1/2001 |
| WO | 2001072214 | 10/2001 |
| WO | 2006028824 | 3/2006 |
| WO | 2007109554 | 9/2007 |
| WO | 2008/028149 A2 | 3/2008 |
| WO | 2008114748 | 9/2008 |
| WO | 2008154578 | 12/2008 |
| WO | 2010075450 | 7/2010 |
| WO | 2011025640 | 3/2011 |
| WO | 2011113162 | 9/2011 |
| WO | 2013/044182 A1 | 3/2013 |
| WO | 2013068885 A1 | 5/2013 |
| WO | 2013116316 | 8/2013 |
| WO | 2014028770 | 2/2014 |
| WO | 2015/077474 A1 | 5/2015 |
| WO | 2015073871 | 5/2015 |
| WO | 2016/073476 | 5/2016 |
| WO | WO 2016/086160 | 6/2016 |
| WO | 2017/015257 A1 | 1/2017 |

OTHER PUBLICATIONS

Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).

PCT International Search Report based on PCT/US15/058851 dated Feb. 4, 2016.

Office Action in U.S. Appl. No. 14/541,991 dated Feb. 28, 2017.

Office Action in U.S. Appl. No. 14/689,475 dated Apr. 13, 2017.

Office Action in U.S. Appl. No. 14/541,991 dated Jul. 13, 2017.

Anderson et al. "Real-time spectroscopic assessment of thermal damage: implications for radiofrequency ablation". J Gastroint Surg. 2004; 8: 660-669.

Asfour et al, "Signal decomposition of transmembrane voltage-sensitive dye fluorescence using a multiresolution wavelet analysis" IEEE Trans Biomed Eng. 2011; 58: 2083-2093.

Boersma et al,."Pulmonary vein isolation by duty-cycled bipolar and unipolar radiofrequency energy with a multielectrode ablation catheter". Heart Rhythm5:1635-1642, 2008.

Buch et al. "Epicardial catheter ablation of atrial fibrillation." Minerva Med. 2009; 100: 151-157.

Cancio et al., "Hyperspectral Imaging: A New Approach to the Diagnosis of Hemorrhagic Shock", The Journal of Trauma, 2006, vol. 60, No. 5: 1087-1095.

Chance et al, "Fluorescence measurements of mitochondrial pyridine nucleotide in aerobiosis and anaerobiosis" Nature. 1959; 184: 931-4.

Coremans et al, "Pretransplantation assessment of renal viability with NADH fluorimetry", Kidney International, vol. 57, (2000), pp. 671-683.

d'Avila A. "Epicardial catheter ablation of ventricular tachycardia." Heart Rhythm. 2008; 5: S73-5.

(56) References Cited

OTHER PUBLICATIONS

Demos et al, "Real time assessment of RF cardiac tissue ablation with optical spectroscopy", Opt Express. 2008; 16: 15286-15296.
Dickfeld et al, "Characterization of Radiofrequency Ablation Lesions With Gadolinium-Enhanced Cardiovascular Magnetic Resonance Imaging" J Am Coll Cardiol. 2006; 47: 370-378.
Dukkipati et al, "Visual balloon-guided point-by-point ablation: reliable, reproducible, and persistent pulmonary vein isolation", Circ Arrhythm Electrophysiol. 2010; 3: 266-273.
Dumas et al, "Myocardial electrical impedance as a predictor of the quality of Re-induced linear lesions." Physiol Meas. 2008; 29: 1195-1207.
Fleming et al, "Real-time monitoring of cardiac redio-frequency ablation lesion formation using an optical coherence tomography forward-imaging catheter", Journal of Biomedical Optics, May/Jun. 2010, vol. 15(3).
Fleming et al, "Toward guidance of epicardial cardiac radiofrequency ablation therapy using optical coherence tomography" J Biomed Opt. 2010; 15: 041510.
Girard et al, "Contrast-enhanced C-arm CT evaluation of radiofrequency ablation lesions in the left ventricle", JACC Cardiovasc Imaging 2011; 4: 259-268.
Grimard et al, "Percutaneous epicardial radiofrequency ablation of ventricular arrhythmias after failure of endocardial approach: a 9-year experience" J Cardiovasc Electrophysiol. 2010; 21: 56-61.
Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.
Himel et al, "Translesion stimulus-excitation delay indicates quality of linear lesions produced by radiofrequency ablation in rabbit hearts", Physiol Meas. 2007; 28: 611-623.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.
Kim et al, "Materials for multifunctional balloon catheters with capabilities in cardiac electrophysiological mapping and ablation therapy", Nat Mater. 2011; 10: 316-323.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial fibrillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed Eng. May 2009; 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.
Roger et al, "American Heart Association Committee and Stoke Subcommittee. Heart disease and stroke statistics—2011 update; a report from the American Heart Association", Circulation 2011; 123: e18-e209.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.
Sosa et al, "Epicardial mapping and ablation techniques to control ventricular tachycardia". J Cardiovasc Electrophysiol. 2005; 16: 449-452.
Swartling et al, "Changes in tissue optical properties due to radio-frequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Van Haesendonck C, Sinnaeve A, Willems R, Vandenbulcke F, Stroobandt R, ."Biophysical and electrical aspects of radiofrequency catheter ablation". Acta Cardiol 50: 105-115, 1995.
Vetterlein et al, "Extent of damage in aschemic, nonreperfused myocardium of anesthetized rats", Am J Physiol Heart Circ Physiol 285: H755-H765, 2003.
Vo-Dinh et al., "A Hyperspectral Imaging System for In Vivo Optical Diagnostics", IEEE Engineering in Medicine and Biology Magazine, pp. 40-49, Sep./Oct. 2004.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.
Office Action in U.S. Appl. No. 13/624,899 dated Oct. 2, 2014.
Office Action in U.S. Appl. No. 13/624,902 dated Oct. 2, 2014.
Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.
Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May 1990.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.
Naito, H., et al., "Use of NADH Fluorescence Imaging for Early Detection of Energy Failure and a Prediction of Infarction", Critical Care Medicine, vol. 39, Issue 12, pp. 40, Dec. 2011.
Smith, S., et al., "Imaging Appearances Following Thermal Ablation", Clinical Radiology, vol. 63, Issue 1, pp. 1-11, Jan. 2008.

(56) References Cited

OTHER PUBLICATIONS

Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.
Swift, L.M., et al., "Properties of Blebbistatin for Cardiac Optical Mapping and Other Imaging Applications", European Journal of Physiology, vol. 464, Issue 5, pp. 503-512, Nov. 2012.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.
European Search Report completed May 26, 2015 for EP 12 83 4435.
International Search Report dated Jan. 19, 2016 for PCT/US2015/058824.
Office Action in U.S. Appl. No. 14/689,475 dated Aug. 23, 2017.
Office Action in U.S. Appl. No. 14/622,477 dated Oct. 5, 2017.
Swift, Luther Mitchell, "Real-Time Visualization of Cardiac Ablation Lesions Using Endogenous NADH Fluorescence and Reflected Light", A dissertation submitted to the Faculty of the Columbian College of Arts and Sciences of the George Washington University in partial fulfillment of the requirements for the degree of Doctor of Philosophy, Jul. 23, 2013.
Office Action in U.S. Appl. No. 14/931,262 dated Apr. 20, 2018.
Office Action in U.S. Appl. No. 14/622,477 dated Jun. 5, 2018.
European Search Report completed Jun. 8, 2018 for EP 15 86 3645.
Office Action in U.S. Appl. No. 14/549,057 dated Jun. 15, 2018.

* cited by examiner

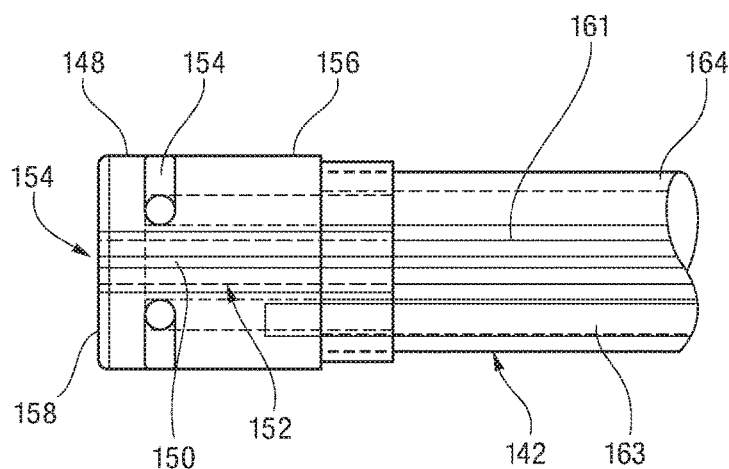
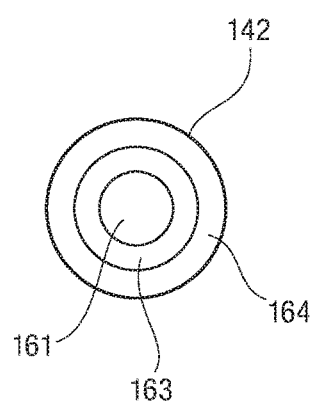
FIG. 2A    FIG. 2B
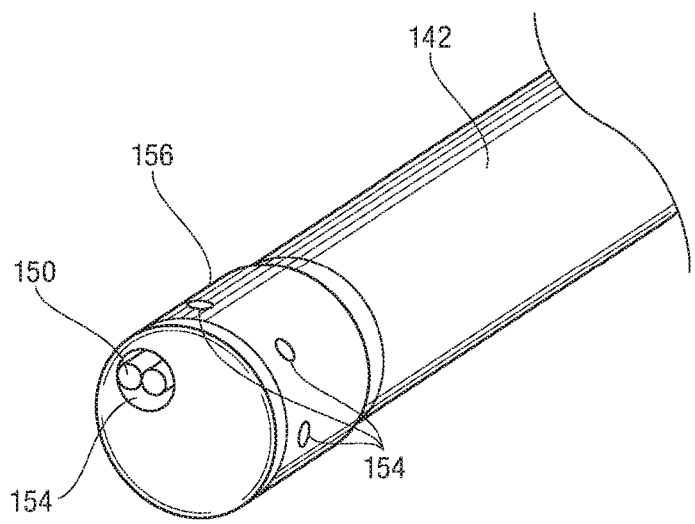
FIG. 2C

SYSTEMS AND METHODS FOR ASSESSMENT OF CONTACT QUALITY

RELATED APPLICATIONS

This application claims the benefit of and priority to U.S. Provisional Application Ser. No. 62/074,615, filed on Nov. 3, 2014, which is incorporated herein by reference in its entirety.

FIELD

The present disclosure generally relates to ablation and visualization systems and methods to access quality of contact between a catheter and tissue.

BACKGROUND

Atrial fibrillation (AF) is the most common sustained arrhythmia in the world, which currently affects millions of people. In the United States, AF is projected to affect 10 million people by the year 2050. AF is associated with increased mortality, morbidity, and an impaired quality of life, and is an independent risk factor for stroke. The substantial lifetime risk of developing AF underscores the public heath burden of the disease, which in the U.S. alone amounts to an annual treatment cost exceeding $7 billion.

Most episodes in patients with AF are known to be triggered by focal electrical activity originating from within muscle sleeves that extend into the Pulmonary Veins (PV). Atrial fibrillation may also be triggered by focal activity within the superior vena cava or other atrial structures, i.e. other cardiac tissue within the heart's conduction system. These focal triggers can also cause atrial tachycardia that is driven by reentrant electrical activity (or rotors), which may then fragment into a multitude of electrical wavelets that are characteristic of atrial fibrillation. Furthermore, prolonged AF can cause functional alterations in cardiac cell membranes and these changes further perpetuate atrial fibrillation.

Radiofrequency ablation (RFA), laser ablation and cryo ablation are the most common technologies of catheter-based mapping and ablation systems used by physicians to treat atrial fibrillation. Physicians use a catheter to direct energy to either destroy focal triggers or to form electrical isolation lines isolating the triggers from the heart's remaining conduction system. The latter technique is commonly used in what is called pulmonary vein isolation (PVI). However, the success rate of the AF ablation procedure has remained relatively stagnant with estimates of recurrence to be as high as 30% to 50% one-year post procedure. The most common reason for recurrence after catheter ablation is one or more gaps in the PVI lines. The gaps are usually the result of ineffective or incomplete lesions that may temporarily block electrical signals during the procedure but heal over time and facilitate the recurrence of atrial fibrillation.

Ineffective or incomplete lesions are often the result of poor catheter contact with the myocardium. With poor contact the transfer of energy from the catheter to the myocardium is inefficient and often insufficient to cause a proper lesion. Intermittent contact can also be unsafe.

Therefore, there is a need for system and method for forming and verifying proper catheter contact and stability to improve outcomes and reduce costs.

SUMMARY

The present disclosure generally relates to ablation and visualization systems and methods to access quality of contact between a catheter and tissue.

According to some aspects of the present disclosure, there is provided a method for monitoring tissue ablation of the present disclosure that includes advancing a distal tip of an ablation catheter to a tissue in need of ablation; illuminating the tissue with UV light to excite NADH in the tissue, wherein the tissue is illuminated in a radial direction, an axial direction, or both; determining from a level of NADH fluorescence in the illuminated tissue when the distal tip of the catheter is in contact with the tissue; and delivering ablation energy to the tissue to form a lesion in the tissue.

According to some aspects of the present disclosure, there is provided a system for monitoring tissue ablation that includes a catheter comprising a catheter body; and a distal tip positioned at a distal end of the catheter body, the distal tip defining an illumination cavity having one or more openings for exchange of light energy between the illumination cavity and tissue; an ablation system in communication with the distal tip to deliver ablation energy to distal tip; a visualization system comprising a light source, a light measuring instrument, and one or more optical fibers in communication with the light source and the light measuring instrument and extending through the catheter body into the illumination cavity of the distal tip, wherein the one or more optical fibers are configured to pass light energy in and out of the illumination chamber; a processor in communication with the ablation energy source, light source and the light measuring instrument, the processor being programmed to receive NADH fluorescence data from a tissue illuminated with UV light through the distal tip of the catheter, wherein the tissue is illuminated in a radial direction, an axial direction, or both; to determine from a level of NADH fluorescence in the illuminated tissue when the distal tip of the catheter is in contact with the tissue; and to cause (either automatically or by prompting the user) delivery of ablation energy to the tissue to form a lesion in the tissue upon determining that the distal tip is in contact with the tissue

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 2A-2E illustrate various embodiments of catheters of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides methods and systems for lesion assessment. In some embodiments, the system of the present disclosure includes a catheter configured to serve two functions: a therapeutic function of delivering ablation therapy to a target tissue and a diagnostic function of gathering a signature spectrum from a point of contact of the catheter and tissue to access lesions. In some embodiments, the systems and methods of the present disclosure may be employed for imaging tissue using nicotinamide adenine dinucleotide hydrogen (NADH) fluorescence (fNADH). In general, the system may include a catheter with an optical system for exchanging light between tissue and the catheter. In some embodiments, the instant systems allow for direct visualization of the tissue's NADH fluorescence, or lack thereof, induced by ultraviolet (UV) excitation. The NADH fluorescence signature returned from the tissue can be used to determine the quality of contact between the tissue and a catheter system.

In some embodiments, the catheter includes an ablation therapy system at its distal end and is coupled to a diagnostic unit comprising a light source, such as a laser, and a spectrometer. The catheter may include one or more fibers extending from the light source and the spectrometer to a distal tip of the catheter to provide illuminating light to the point of contact between the catheter and tissue and to receive and deliver a signature NADH spectrum from the point of contact to the spectrometer. The signature NADH spectrum may be used to assess lesion in the target tissue. In some embodiments, the methods of the present disclosure include illuminating a tissue having a lesion, receiving a signature spectrum of the tissue, and performing a qualitative assessment of the lesion based on the signature spectrum from the tissue. The analysis can occur in real-time before, during and after ablation lesion formation. It should be noted that while the systems and methods of the present disclosure are described in connection with cardiac tissue and NADH spectrum, the systems and methods of the present disclosure may be used in connection with other types of tissue and other types of fluorescence.

System: Diagnostic Unit

Figure 1A:
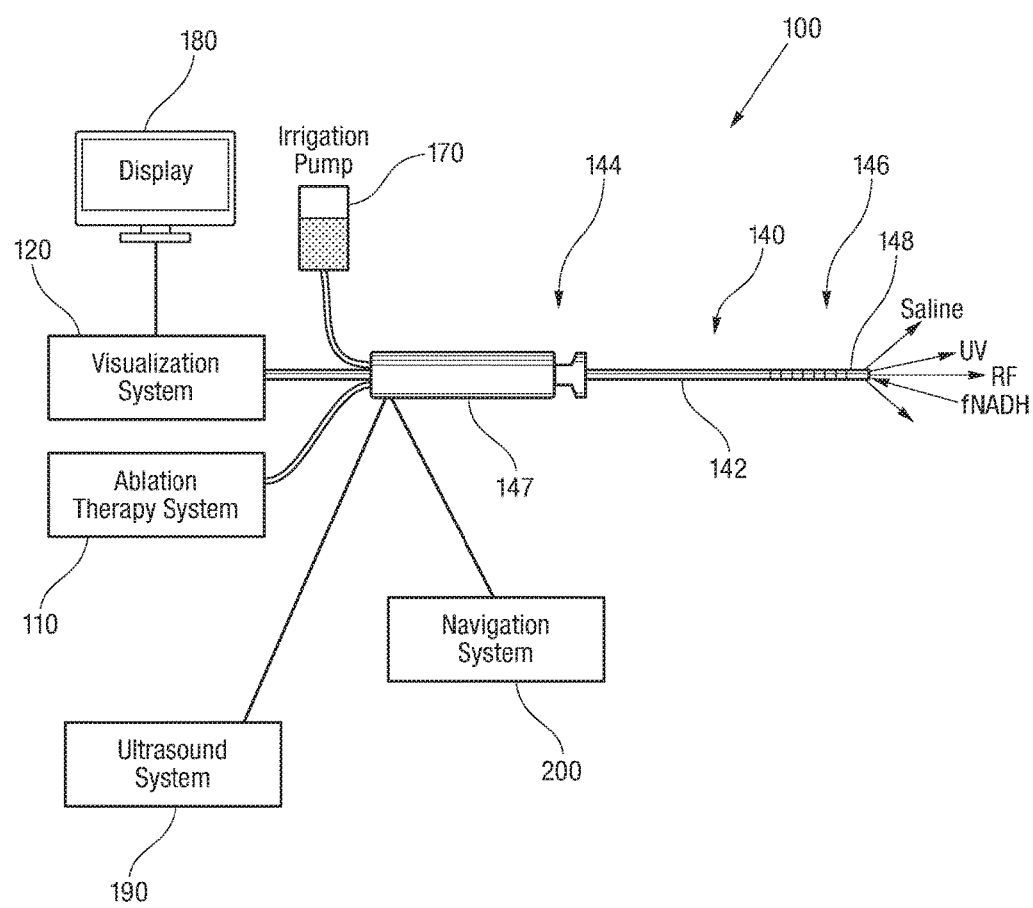
FIG. 1A illustrates an embodiment of an ablation visualization and monitoring system of the present disclosure.

In reference to FIG. 1A, the system for providing ablation therapy 100 may include an ablation therapy system 110, a visualization system 120, and a catheter 140. In some embodiments, the system 100 may also include one or more of an irrigation system 170, ultrasound system 190 and a navigation system 200. The system may also include a display 180, which can be a separate display or a part of the visualization system 120, as described below. In some embodiments, the system includes an RF generator, an irrigation pump 170, an irrigated-tip ablation catheter 140, and the visualization system 120.

In some embodiments, the ablation therapy system 110 is designed to supply ablation energy to the catheter 140. The ablation therapy system 110 may include one or more energy sources that can generate radiofrequency (RF) energy, microwave energy, electrical energy, electromagnetic energy, cryoenergy, laser energy, ultrasound energy, acoustic energy, chemical energy, thermal energy or any other type of energy that can be used to ablate tissue. In some embodiments, the catheter 140 is adapted for an ablation energy, the ablation energy being one or more of RF energy, cryo energy, laser, chemical, electroporation, high intensity focused ultrasound or ultrasound, and microwave.

Figure 1B:
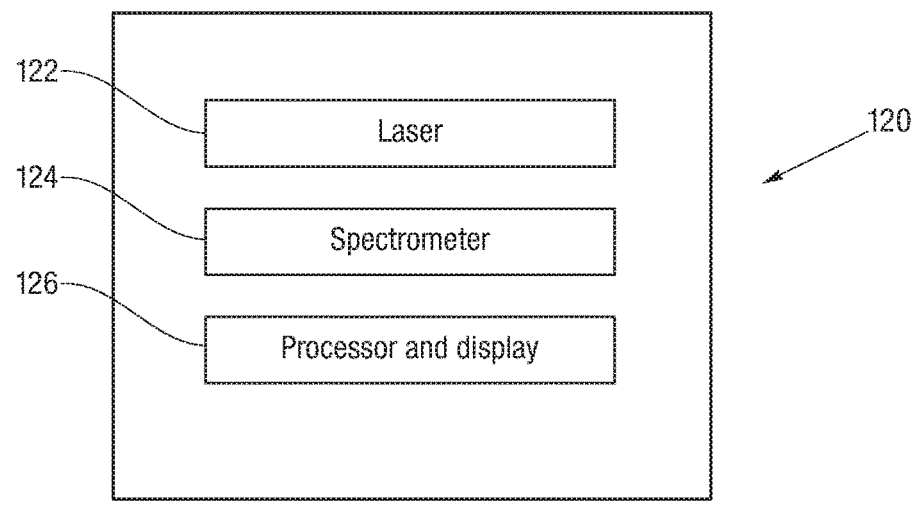
FIG. 1B is a diagram of an embodiment of a visualization system for use in connection with an ablation visualization and monitoring system of the present disclosure.

In reference to FIG. 1B, the visualization system 120 may include a light source 122, a light measuring instrument 124, and a computer system 126.

In some embodiments, the light source 122 may have an output wavelength within the target fluorophore (NADH, in some embodiments) absorption range in order to induce fluorescence in healthy myocardial cells. In some embodiments, the light source 122 is a solid-state laser that can generate UV light to excite NADH fluorescence. In some embodiments, the wavelength may be about 355 nm or 355 nm+/−30 nm. In some embodiments, the light source 122 can be a UV laser. Laser-generated UV light may provide much more power for illumination and may be more efficiently coupled into a fiber-based illumination system, as is used in some embodiments of the catheter 140. In some embodiments, the instant system can use a laser with adjustable power up to 150 mW.

The wavelength range on the light source 122 may be bounded by the anatomy of interest, a user specifically choosing a wavelength that causes maximum NADH fluorescence without exciting excessive fluorescence of collagen, which exhibits an absorption peak at only slightly shorter wavelengths. In some embodiments, the light source 122 has a wavelength from 300 nm to 400 nm. In some embodiments, the light source 122 has a wavelength from 330 nm to 370 nm. In some embodiments, the light source 122 has a wavelength from 330 nm to 355 nm. In some embodiments, a narrow-band 355 nm source may be used. The output power of the light source 122 may be high enough to produce a recoverable tissue fluorescence signature, yet not so high as to induce cellular damage. The light source 122 may be coupled to an optical fiber to deliver light to the catheter 140, as will be described below.

In some embodiments, the systems of the present disclosure may utilize a spectrometer as the light measuring instrument 124, but other light measuring instruments may be employed.

The optical fiber can deliver the gathered light to a long pass filter that blocks the reflected excitation wavelength of 355 nm, but passes the fluoresced light that is emitted from the tissue at wavelengths above the cutoff of the filter. The filtered light from the tissue can then be captured and analyzed by the light measuring instrument 124. The computer system 126 acquires the information from the light measuring instrument 124 and displays it to the physician.

Referring back to FIG. 1A, in some embodiments, the system 100 of the present disclosure may further include an ultrasound system 190. The catheter 140 may be equipped with ultrasound transducers in communication with the ultrasound system 190. In some embodiments, the ultrasound may show tissue depths, which in combination with the metabolic activity or the depth of lesion may be used to determine if a lesion is in fact transmural or not. In some embodiments, the ultrasound transducers may be located in the distal section of the catheter 140, and optionally in the tip of the distal electrode. The ultrasonic transducers may be configured to assess a tissue thickness either below or adjacent to the catheter tip. In some embodiments, the catheter 140 may comprise multiple transducers adapted to provide depth information covering a situation where the catheter tip is relatively perpendicular to a myocardium or relatively parallel to a myocardium.

Referring to FIG. 1A, as noted above, the system 100 may also include an irrigation system 170. In some embodiments, the irrigation system 170 pumps saline into the catheter 140 to cool the tip electrode during ablation therapy. This may help to prevent steam pops and char (i.e. clot that adheres to the tip that may eventually dislodge and cause a thrombolytic event) formation. In some embodiments, the irrigation fluid is maintained at a positive pressure relative to pressure outside of the catheter 140 for continuous flushing of the one or more openings 154.

Referring to FIG. 1A, the system 100 may also include a navigation system 200 for locating and navigating the catheter 140. In some embodiments, the catheter 140 may include one or more electromagnetic location sensors in communication with the navigation system 200. In some embodiments, the electromagnetic location sensors may be used to locate the tip of the catheter in the navigation system 200. The sensor picks up electromagnetic energy from a source location and computes location through triangulation or other means. In some embodiments the catheter 140 comprises more than one transducer adapted to render a position of the catheter body 142 and a curvature of the catheter body on a navigation system display. In some embodiments, the navigation system 200 may include one or more magnets and alterations in the magnetic field produced by the magnets on the electromagnetic sensors can deflect the tip of catheters to the desired direction. Other navigation systems may also be employed, including manual navigation.

Figure 1C:
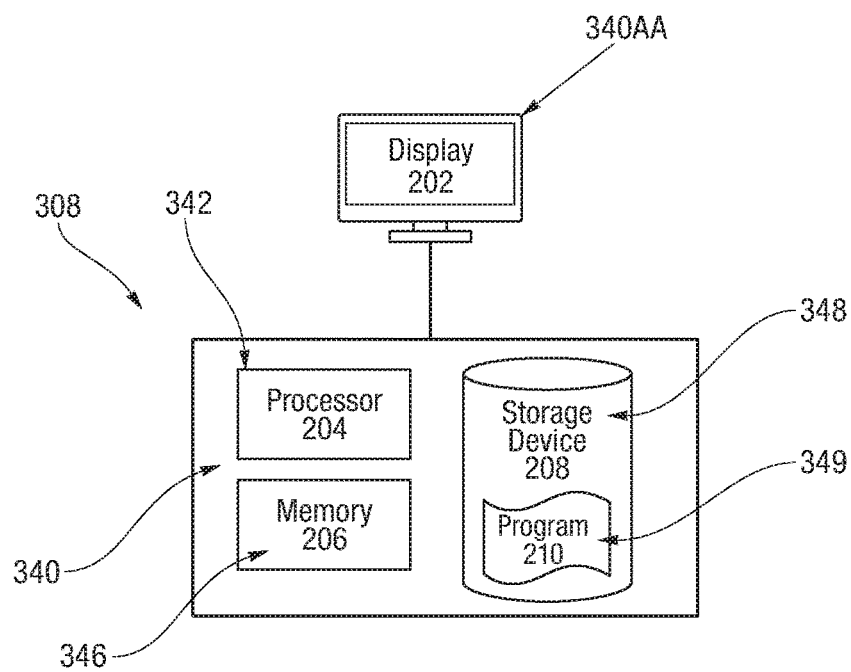
FIG. 1C illustrates an exemplary computer system suitable for use in connection with the systems and methods of the present disclosure.

The computer system 126 can be programmed to control various modules of the system 100, including, for example, control over the light source 122, control over the light measuring instrument 124, execution of application specific software, control over ultrasound, navigation and irrigation systems and similar operations. FIG. 1C shows, by way of example, a diagram of a typical processing architecture 308, which may be used in connection with the methods and systems of the present disclosure. A computer processing device 340 can be coupled to display 340AA for graphical output. Processor 342 can be a computer processor 342 capable of executing software. Typical examples can be computer processors (such as Intel® or AMD®, processors), ASICs, microprocessors, and the like. Processor 342 can be coupled to memory 346, which can be typically a volatile RAM memory for storing instructions and data while processor 342 executes. Processor 342 may also be coupled to storage device 348, which can be a non-volatile storage medium, such as a hard drive, FLASH drive, tape drive, DVDROM, or similar device. Although not shown, computer processing device 340 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 340. Processor 342 may also be coupled to other type of computer-readable media, including, but are not limited to, an electronic, optical, magnetic, or other storage or transmission device capable of providing a processor, such as the processor 342, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Program 349 can be a computer program or computer readable code containing instructions and/or data, and can be stored on storage device 348. The instructions may comprise code from any computer-programming language, including, for example, C, C++, C#, Visual Basic, Java, Python, Perl, and JavaScript. In a typical scenario, processor 204 may load some or all of the instructions and/or data of program 349 into memory 346 for execution. Program 349 can be any computer program or process including, but not limited to web browser, browser application, address registration process, application, or any other computer application or process. Program 349 may include various instructions and subroutines, which, when loaded into memory 346 and executed by processor 342 cause processor 342 to perform various operations, some or all of which may effectuate the methods for managing medical care disclosed herein. Program 349 may be stored on any type of non-transitory computer readable medium, such as, without limitation, hard drive, removable drive, CD, DVD or any other type of computer-readable media.

In some embodiments, the computer system may be programmed to perform the steps of the methods of the present disclosure and control various parts of the instant systems to perform necessary operation to achieve the methods of the present disclosure. In some embodiments, the processor may be programmed to receive NADH fluorescence data from a tissue illuminated with UV light through the distal tip of the catheter, wherein the tissue is illuminated in a radial direction, an axial direction, or both; to determine from a level of NADH fluorescence in the illuminated tissue when the distal tip of the catheter is in contact with the tissue; and to cause (either automatically or by prompting the user) delivery of ablation energy to the tissue to form a lesion in the tissue upon determining that the distal tip is in contact with the tissue.

The processor may further be programmed monitoring the level of NADH fluorescence during the delivering ablation energy to confirm that the distal tip remains in contact with the tissue. In some embodiments, monitoring the level of NADH fluorescence during the delivering ablation energy may be utilized to determine stability of contact between the distal tip and the tissue. In some embodiments, ablation of the tissue may be stopped when the contact between the distal tip and the tissue is not stable. In some embodiments, the processor may further be programmed to collect a spectrum of fluorescence light reflected from the illuminated tissue to distinguish tissue type.

In some embodiments, the tissue is illuminated with light having a wavelength between about 300 nm and about 400 nm. In some embodiments, a level of the reflected light having a wavelength between about 450 nm and 470 nm is monitored. In some embodiments, the monitored spectrum may be between 410 nm and 520 nm. Additionally or alternatively, a wider spectrum may be monitored, such as, by way of a non-limiting example, between 375 nm and 575 nm. In some embodiments, the NADH fluorescence spectrum and a wider spectrum may be displayed to user simultaneously. In some embodiments, the lesion may be created by ablation energy selected from the group consisting of radiofrequency (RF) energy, microwave energy, electrical energy, electromagnetic energy, cryoenergy, laser energy, ultrasound energy, acoustic energy, chemical energy, thermal energy and combinations thereof. In some embodiments, the procedure may be started (by the processor or by prompting the user by the processor) when a NADH fluorescence peak is detected so it can be monitored throughout the procedure. As noted above, the processor may perform these methods in combination with other diagnostic methods, such as ultrasound monitoring.

System: Catheter

The catheter 140 may be based on a standard ablation catheter with accommodations for the optical fibers for illumination and spectroscopy, as discussed above. In some embodiments, the catheter 140 is a steerable, irrigated RF ablation catheter that can be delivered through a sheath to the endocardial space via a standard transseptal procedure and common access tools. On the handle of the catheter 147, there may be connections for the standard RF generator and irrigation system 170 for therapy. The catheter handle 147 also passes the optical fibers that are then connected to the diagnostic unit to obtain the tissue measurements.

Referring back to FIG. 1A, the catheter 140 includes a catheter body 142 having a proximal end 144 and a distal end 146. The catheter body 142 may be made of a biocompatible material, and may be sufficiently flexible to enable steering and advancement of the catheter 140 to a site of ablation. In some embodiments, the catheter body 142 may have zones of variable stiffness. For example, the stiffness of the catheter 140 may increase from the proximal end 144 toward the distal end 146. In some embodiments, the stiffness of the catheter body 142 is selected to enable delivery of the catheter 140 to a desired cardiac location. In some embodiments, the catheter 140 can be a steerable, irrigated radiofrequency (RF) ablation catheter that can be delivered through a sheath to the endocardial space, and in the case of the heart's left side, via a standard transseptal procedure using common access tools. The catheter 140 may include a handle 147 at the proximal end 144. The handle 147 may be in communication with one or more lumens of the catheter to allow passage of instruments or materials through the catheter 140. In some embodiments, the handle 147 may include connections for the standard RF generator and irrigation system 170 for therapy. In some embodiments, the catheter 140 may also include one more adaptors configured to accommodate the optical fiber for illumination and spectroscopy.

In reference to FIG. 1A, at the distal end 146, the catheter 140 may include a distal tip 148, having a side wall 156 and a front wall 158. The front wall 158 may be, for example, flat, conical or dome shaped. In some embodiments, the distal tip 148 may be configured to act as an electrode for diagnostic purposes, such as for electrogram sensing, for therapeutic purposes, such as for emitting ablation energy, or both. In some embodiments where ablation energy is required, the distal tip 148 of the catheter 140 could serve as an ablation electrode or ablation element.

In the embodiments where RF energy is implemented, the wiring to couple the distal tip 148 to the RF energy source (external to the catheter) can be passed through a lumen of the catheter. The distal tip 148 may include a port in communication with the one or more lumens of the catheter. The distal tip 148 can be made of any biocompatible material. In some embodiments, if the distal tip 148 is configured to act as an electrode, the distal tip 148 can be made of metal, including, but not limited to, platinum, platinum-iridium, stainless steel, titanium or similar materials.

In reference to FIG. 2A, an optical fiber or an imaging bundle 150 may be passed from the visualization system 120, through the catheter body 142, and into an illumination cavity or compartment 152, defined by the distal tip 148. The distal tip 148 may be provided with one or more openings 154 for exchange of light energy between the illumination cavity 152 and tissue. In some embodiments, even with multiple openings 154, the function of the distal tip 148 as an ablation electrode is not compromised. The openings may be disposed on the front wall 156, on the side wall 158 or both. The openings 154 may also be used as irrigation ports. The light is delivered by the fiber 150 to the distal tip 148, where it illuminates the tissue in the proximity of the distal tip 148. This illumination light is either reflected or causes the tissue to fluoresce. The light reflected by and fluoresced from the tissue may be gathered by the optical fiber 150 within the distal tip 148 and carried back to the visualization system 120. In some embodiments, the same optical fiber or bundle of fibers 150 may be used to both direct light to the illumination chamber of the distal tip to illuminate tissue outside the catheter 140 and to collect light from the tissue.

In reference to FIG. 2A, in some embodiments, the catheter 140 may have a visualization lumen 160 through which the optical fiber 150 may be advanced through the catheter body 142. The optical fiber 150 may be advanced through the visualization lumen 161 into the illumination cavity 152 to illuminate the tissue and receive reflected light through the opening 154. As necessary, the optical fiber 150 may be advanced beyond the illumination cavity 152 through the opening 154.

As shown in FIG. 2A and FIG. 2B, in addition to the visualization lumen 161, the catheter 140 may further include an irrigation lumen 163 for passing irrigation fluid from the irrigation system 170 to the openings 154 (irrigation ports) in the distal tip 148 and an ablation lumen 164 for passing ablation energy from the ablation therapy system 110 to the distal tip 148, such as, for example, by passing a wire through the ablation lumen 164 for RF ablation energy. It should be noted that the lumens of the catheter may be used for multiple purposes and more than one lumen may be used for the same purpose. In addition, while FIG. 2A and FIG. 2B show the lumens being concentric other configurations of lumens may be employed.

As shown in FIG. 2A and FIG. 2B, in some embodiments, a central lumen of the catheter may be utilized as the visualization lumen 161. In some embodiments, as shown in FIG. 2C, the visualization lumen 161 may be off set in relation to the central access of the catheter 140.

In some embodiments, the light may also be directed radially out of the openings 154 in the side wall 156, alternatively or additionally to being directed through the opening in the front wall 158. In this manner, the light energy exchange between the illumination cavity 152 and tissue may occur over multiple paths, axially, radially or both with respect to the longitudinal central axis of the catheter, as shown in FIG. 2E. This is useful when the anatomy will not allow the catheter tip to be orthogonal to the target site. It may also be useful when increased illumination is required. In some embodiments, additional optical fibers 150 may be used and may be deflected in the radial direction with respect to the catheter 140 to allow the illumination and returned light to exit and enter along the length of the catheter.

Figure 2D:
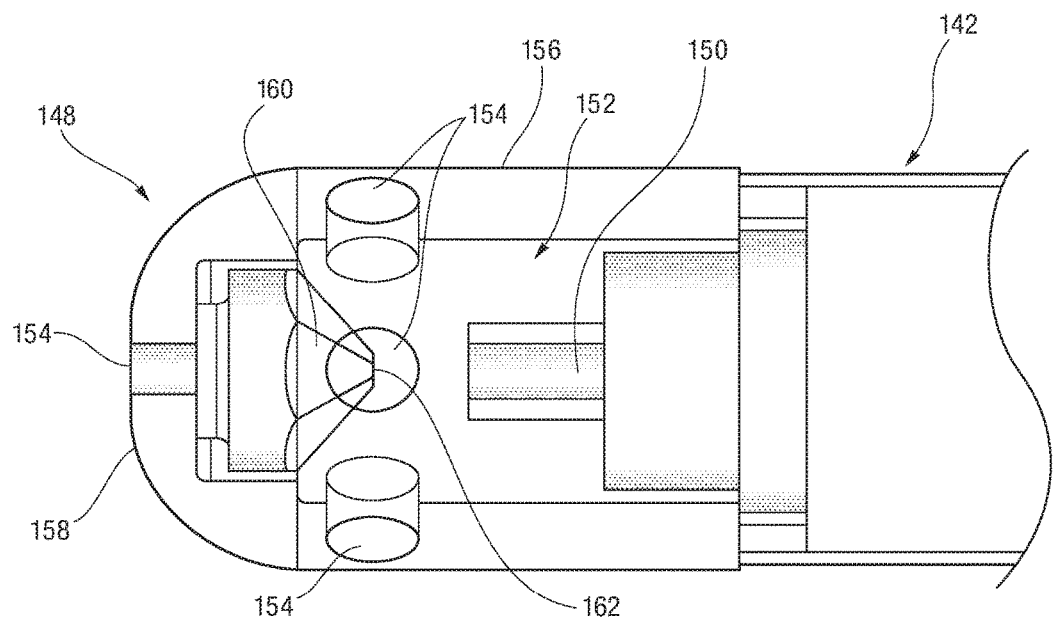
Figure 2E:
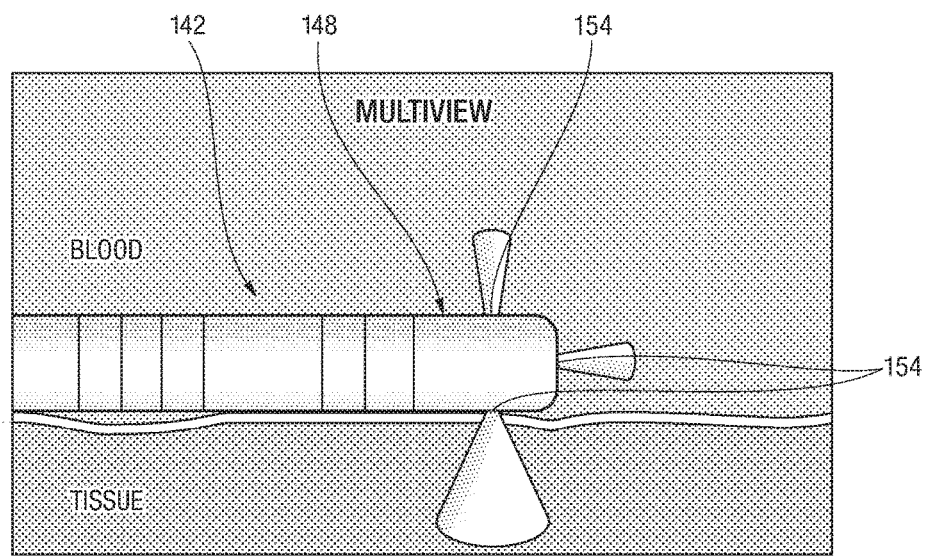

In reference to FIG. 2D, to enable the light energy exchange between the illumination cavity 152 and tissue over multiple paths (axially and radially with respect to the longitudinal central axis of the catheter), a light directing member 160 may be provided in the illumination cavity 152. The light directing member 160 may direct the illumination light to the tissue and direct the light returned through the one or more openings 154 within the distal tip 148 to the optical fiber 150. The light directing member 160 may also be made from any biocompatible material with a surface that reflects light or can be modified to reflect light, such as for example, stainless steel, platinum, platinum alloys, quartz, sapphire, fused silica, metallized plastic, or other similar materials. The light directing member 160 may be conical (i.e. smooth) or faceted with any number of sides. The light directing member 160 may be shaped to bend the light at any desired angle. In some embodiments, the light directing member 160 may be shaped to reflect the light only through the one or more openings. In some embodiments, the light directing member 160 may include 3 or 4 equidistant facets, although more or less facets may be used. In some embodiments, the number of facets may correspond to the number of the openings 154 in the side wall 156. In some embodiments, there may be fewer facets than the openings 154 in the side wall 156. In some embodiments, the facets may be positioned at 45 degrees relative to central axis of the light directing member 160 (135 degrees relative to the axis of the catheter). In some embodiments, the facets 166 may be positioned at greater or lesser angles than 45 degrees in order to direct light more distally or more proximally.

In some embodiments, the material for the light directing member 160 is chosen from materials that do not fluoresce when exposed to illumination between 310 nm to 370 nm. In some embodiments, as shown in FIG. 2D, the light directing member 160 may include one or more holes 162 through the centerline of the mirror, which allow illumination and reflected light to pass in both directions axially, directly in line with the catheter 140. Such an axial path may be useful when the distal-most surface of the distal tip 148 is in contact with the anatomy. The alternate radial paths, as shown in FIG. 2E, may be useful when the anatomy will not allow the distal-most surface of the distal tip 148 to be in contact with the target site as is sometimes the case in the left atrium of the patient during pulmonary vein isolation procedures, common in treating atrial fibrillation. In some embodiments, in all pathways, lensing may not be required and the optical system is compatible with the irrigation system 170 as the light passes through the cooling fluid, which is often saline. The irrigation system 170 may also serve to flush the blood from the holes 162, thus keeping the optical components clean.

Methods of Use

In some embodiments, methods for monitoring tissue ablation are provided. Such methods may provide a real time visual feedback on various factors that can impact lesion formation by displaying the level of NADH fluorescence, as is described below.

In some embodiments, methods for monitoring tissue ablation of the present disclosure comprise advancing a distal tip of an ablation catheter to a tissue in need of ablation; illuminating the tissue with UV light to excite NADH in the tissue, wherein the tissue is illuminated in a radial direction, an axial direction, or both; determining from a level of NADH fluorescence in the illuminated tissue when the distal tip of the catheter is in contact with the tissue; and, upon establishing such contact, delivering ablation energy to the tissue to form a lesion in the tissue. The methods may further comprise monitoring the level of NADH fluorescence during the delivering ablation energy to confirm that the distal tip remains in contact with the tissue. In some embodiments, monitoring the level of NADH fluorescence during the delivering ablation energy may be utilized to determine stability of contact between the distal tip and the tissue. In some embodiments, ablation of the tissue may be stopped when the contact between the distal tip and the tissue is not stable. In some embodiments, the methods further include collecting a spectrum of fluorescence light reflected from the illuminated tissue to distinguish tissue type.

In some embodiments, the tissue is illuminated with light having a wavelength between about 300 nm and about 400 nm. In some embodiments, a level of the reflected light having a wavelength between about 450 nm and 470 nm is monitored. In some embodiments, the monitored spectrum may be between 410 nm and 520 nm. Additionally or alternatively, a wider spectrum may be monitored, such as, by way of a non-limiting example, between 375 nm and 575 nm. In some embodiments, the lesion may be created by ablation energy selected from the group consisting of radiofrequency (RF) energy, microwave energy, electrical energy, electromagnetic energy, cryoenergy, laser energy, ultrasound energy, acoustic energy, chemical energy, thermal energy and combinations thereof. In some embodiments, the methods may be started when a NADH fluorescence peak is detected so it can be monitored throughout the procedure. As noted above, these methods may be used in combination with other diagnostic methods, such as ultrasound monitoring.

Contact Assessment

Figure 3:
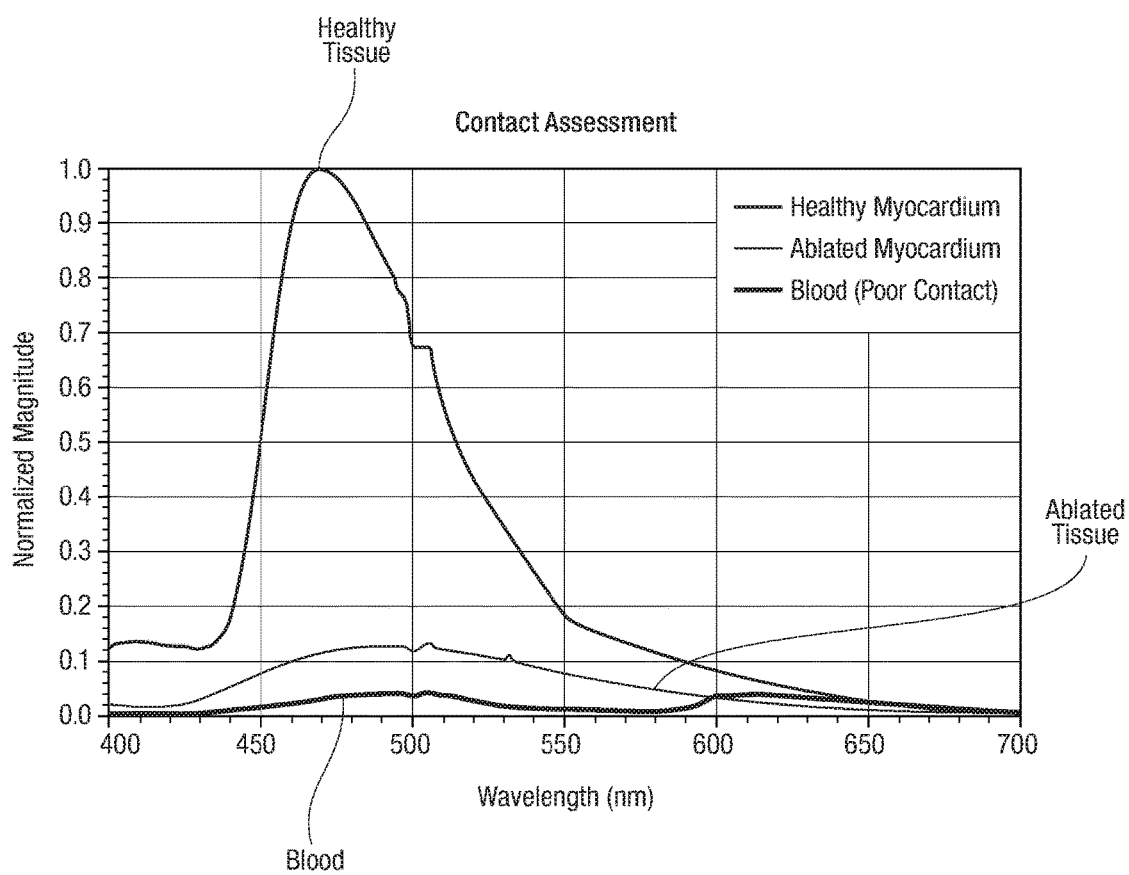
FIG. 3 illustrates exemplary fluorescence spectral plots for monitoring contact between a catheter and tissue according to the present disclosure.
Figure 4:
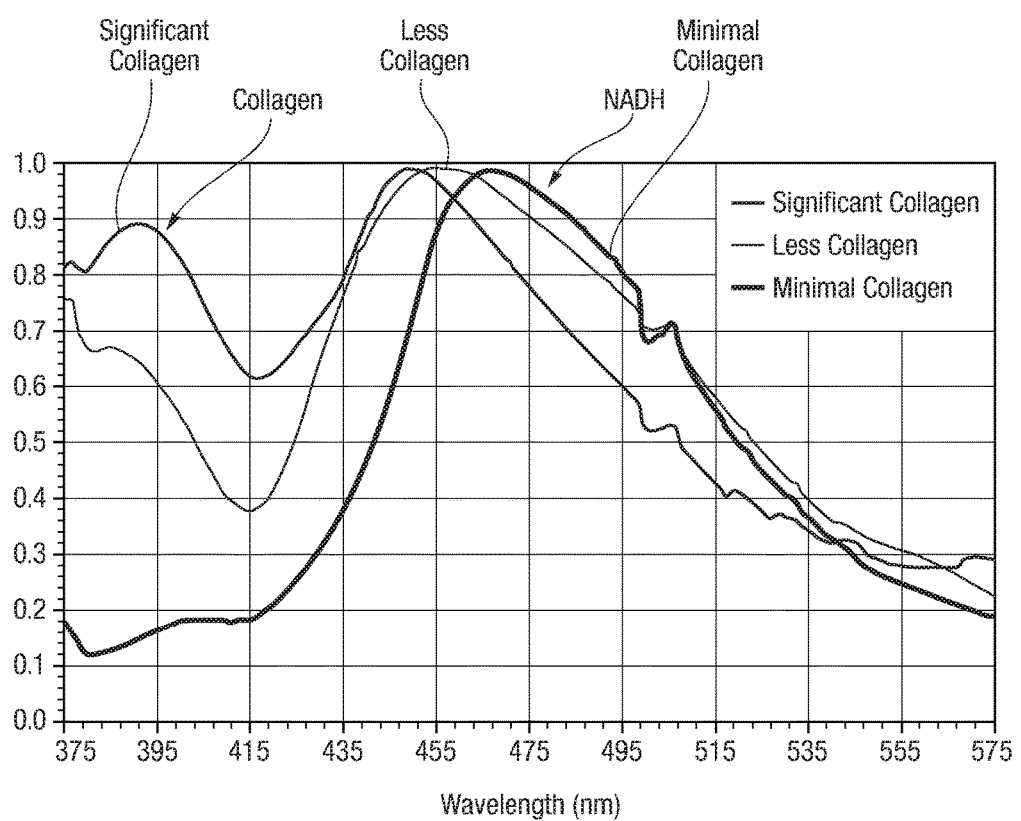
FIG. 4 illustrates exemplary spectral plots of various tissue compositions.

As the tip of the catheter comes into contact with anatomical structures, such as the endocardial or epicardial myocardium, characteristics and the state of the tissue are revealed in the returned spectrum. As shown in FIG. 3, the spectrum between 400 nm and 600 nm is different for blood (low amplitudes), previously ablated tissue, and healthy tissue. When illuminated with 355 nm wavelength, the signature of the healthy tissue is dominated by NADH fluorescence at wavelengths from 400 nm and 600 nm and centered on about 460 nm-470 nm. This may be helpful to determine when the catheter is properly positioned and in contact with the tissue in need of ablation. Moreover, pushing the catheter further against the surface may result in an elevated fluorescence and the spectral signature shifts above the baseline. The use of such feedback may help reduce the risk of perforation during catheter ablation and manipulation, and can help avoid ablation at sub-optimal tissue contact sites and hence decrease RF ablation time In reference to FIG. 4, in some embodiments, the spectral signature may be collected over a broader spectrum. For example, the spectral pattern of collagenous tissue is different than the one seen on healthy myocardium. When illuminated in this case with a 355 nm UV light source, the peak of the spectrum shifts to the left (from about 470 nm to about 445 nm) when imaging over collagenous tissue to shorter wavelengths due to increased effect of collagen fluorescence. This may be used by the user to identify the area that is being treated as being mostly myocardium or being covered by collagen, which is harder to ablate.

In some embodiments, the spectral signature may be monitored to determine catheter stability and actions during lesion formation.

Figure 5A:
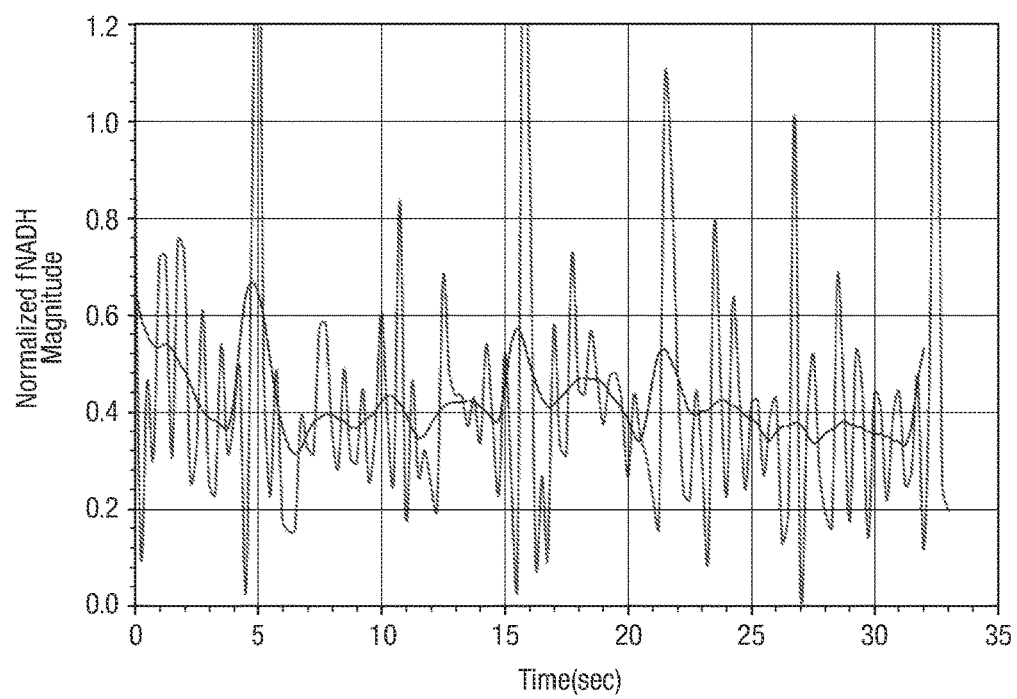
FIG. 5A and FIG. 5B illustrate exemplary fluorescence spectral plots for monitoring stability of a catheter according to the present disclosure.
Figure 5B:
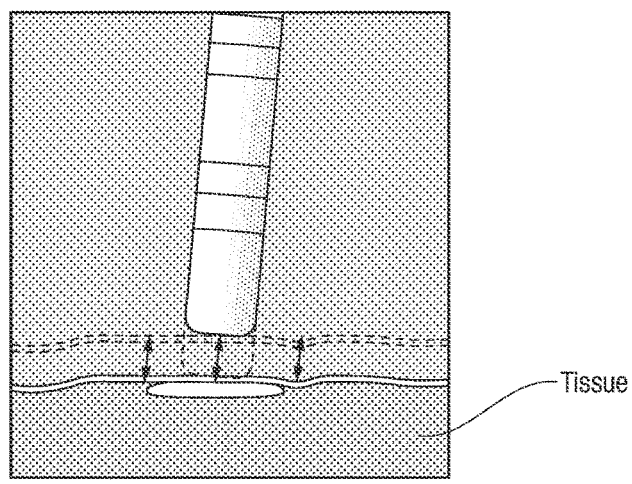

In reference to FIG. 5A and FIG. 5B, an example of intermittent contact of the catheter and the myocardium is shown. As the catheter bounces up and down off of the myocardium, the amplitude of the fNADH signal varies over time, as indicated by a noisy spectral signature. Such spectral signature would indicate poor contact stability. On the other hand, a smooth response corresponds to a stable catheter, as the gradual reduction in fNADH intensity indicates the formation of the ablation lesion over time.

Figure 6A:
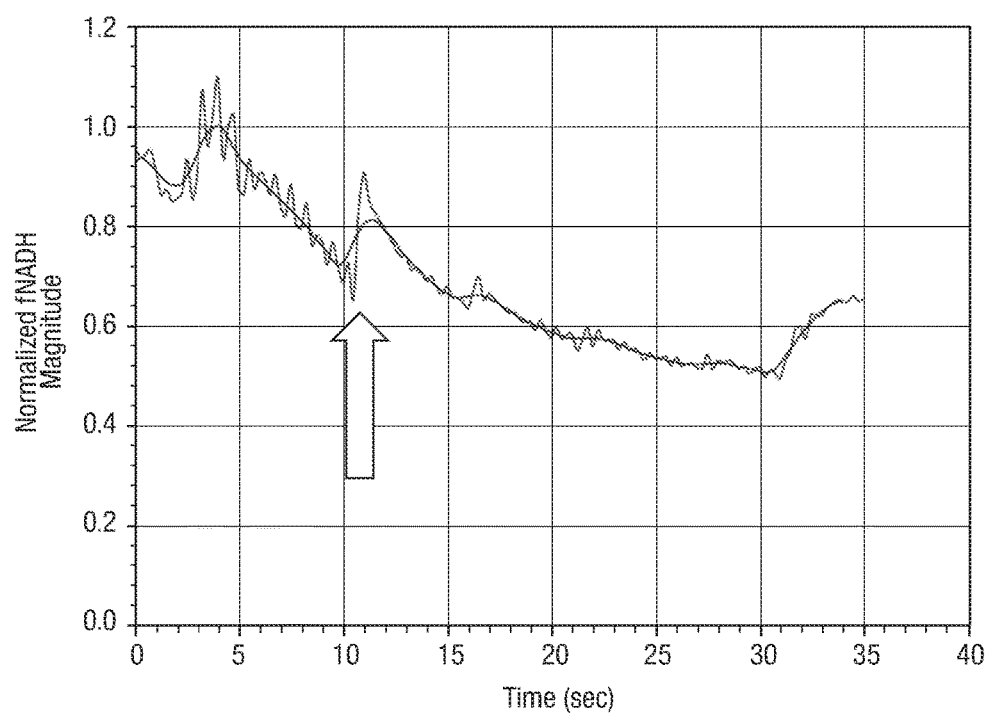
FIG. 6A and FIG. 6B illustrate exemplary fluorescence spectral plots for monitoring stability of a catheter according to the present disclosure.
Figure 6B:
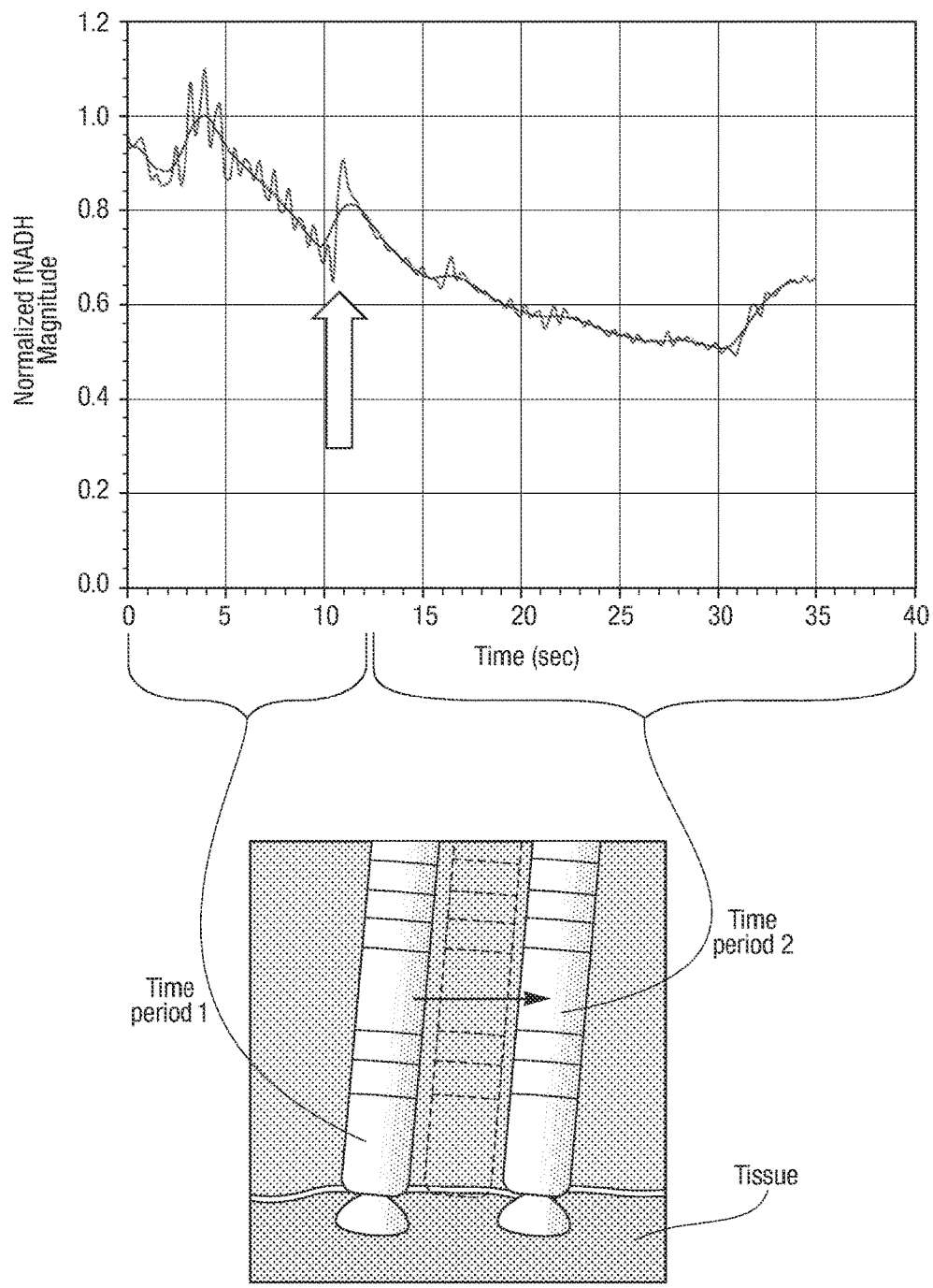

In reference to FIG. 6A and FIG. 6B, the amplitude of the fNADH is relatively smooth over the duration of the application of RF energy in time period 1. The time period 1 also shows a decrease in the fNADH, which indicates successful lesion formation, as the ablated tissue has less or no fNADH, as described above. However, as the catheter is dragged while RF energy is being applied to form a linear lesion, there is a new peak in the fNADH as the ablation tip of the catheter encounters new and unablated myocardium. It is then stable from this point and the reduction in signal amplitude shows the effect of the RF energy on the myocardium There are potential benefits associated with the information content of the returned spectrum to the physician during the ablation procedure. Analysis of the optical signatures that show significant amplitudes in the 375 nm to 600 nm range can correlate to better catheter contact with the myocardium and thus improve the quality of the specific ablation lesion and therefore improve procedure outcomes. The technique of coupling light into tissue from a catheter or specifically an ablation electrode at the distal tip of a catheter can be used to determine and assess the quality of contact that the catheter or the electrode has with the tissue. In addition, knowing more information about the type of tissue being ablated, or whether or not the presence, and possibly the degree, of collagen in said tissue to be ablated ahead of ablation energy deployment may affect the ablation strategy and technique used by the physician for optimal creation of that lesion. For example, in the presence of collagen, a physician may elect one ablation energy source over another (laser over cryo or cryo over RF) and the power or duration or temperature limits may be adjusted higher to achieve a deeper lesion given the collagenous nature of the tissue being ablated.

The instant system allows the physician to have confidence that the energy amount selected will be safe but effective. Allowing the physician to directly assess contact during the entire delivery of ablation energy to create a lesion helps the physician ensure that the catheter has not moved off the tissue during the lesion creation which may present a challenge given the austere environment of continuous motion that the heart endures while beating. The optical property changes of the tissue during ablation are excellent indicators of the amount of energy being delivered to and absorbed by the tissue. Non-obvious changes of the tissue during ablation as well as immediately after ablation energy delivery cessation include how the tissue absorbs delivered light as well as how it scatters it, reacts to it and sends light back (or doesn't, in the case of NADH fluorescence).

Comparison to Impedance

Figure 7:
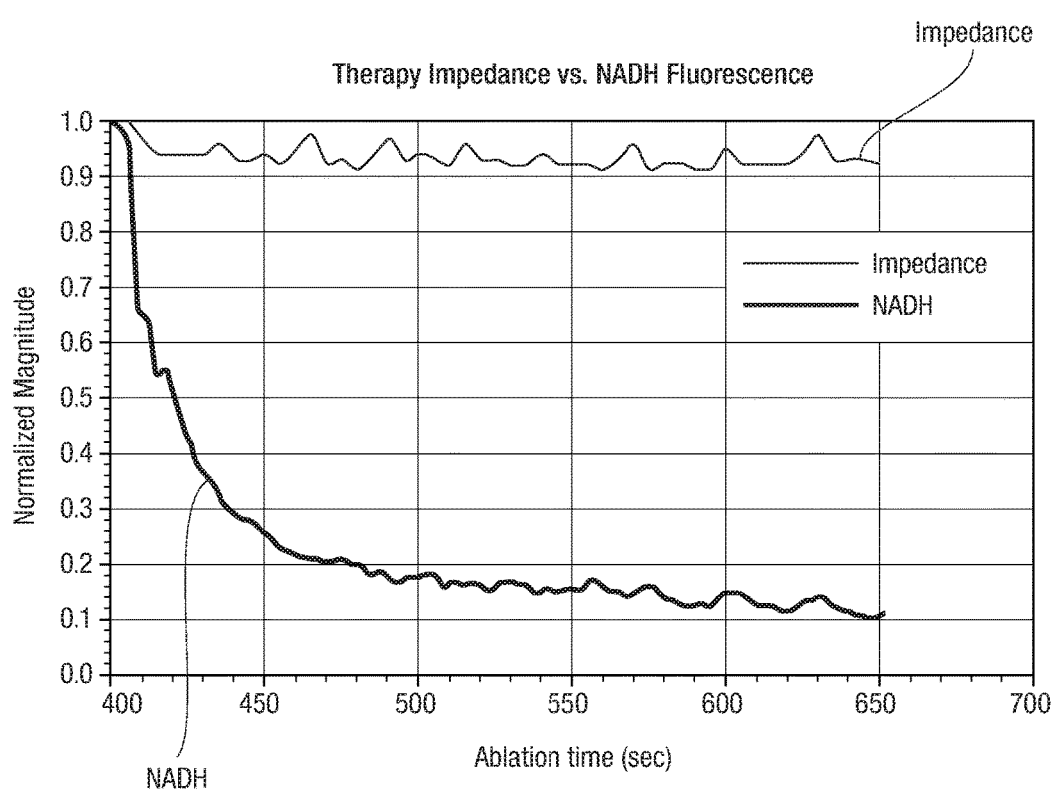
FIG. 7 is a graph comparing fNADH and Impedance over time during an application of ablation energy.

By way of a non-limiting example, FIG. 7 contrasts the fNADH response and therapy impedance over the duration of lesion formation. Impedance is a standard indicator used during ablation procedures throughout the world. It is typically measured from the tip of the catheter to the ablation ground pad adhered to the patient's torso. Physicians expect to see a drop of approximately 10 to 15 ohms in the first 2 or 3 seconds after the onset of ablation energy. If the impedance does not drop, the physician knows that this is likely due to poor catheter contact with the myocardium and the lesion attempt is aborted and the catheter repositioned. The methods described above may be used to ensure better contact between the catheter and the tissue. If the impedance does drop and maintain a new level, the physician continues applying lesion-forming energy typically for a fixed time (30 to 60 seconds or more). If the impedance rises over time, it is an indicator of potential overheating at the tip of the catheter and if unabated can result in dangerous situations of steam formation resulting in cardiac wall rupture or char buildup on the tip of the catheter that could dislodge and become an embolic body.

Returning to FIG. 7, the signal-to-noise ratio (SNR) of the fNADH optical response as compared to therapy impedance SNR would suggest that fNADH is a good indicator of catheter contact. The change in amplitude of the fNADH magnitude is approximately 80% where the same drop in normalized impedance is less than 10%. This comparison of optical signature to impedance also indicates a more direct reflection of the activity in the tissue relative to impedance since the impedance often is a much larger reflection of the electrical path from the electrode to the ground pad through the blood pool. Using the optical approach, all of the light signature is from the tissue and none originates from the blood pool if good contact is maintained. As such, the optical signature is much more highly reflective of the activity in the tissue than the impedance signature.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof. All references cited in this application are incorporated herein by reference in their entireties.

What is claimed is:

1. A method for monitoring tissue ablation comprising:
    advancing a distal tip of an ablation catheter to a tissue in need of ablation;
    illuminating the tissue to excite nicotinamide adenine dinucleotide hydrogen (NADH) in the tissue;
    delivering ablation energy to the tissue to form a lesion in the tissue;
    receiving an NADH fluorescence signal during the delivering ablation energy; and
    displaying an amplitude of the NADH fluorescence signal during the delivering ablation energy, wherein the amplitude of the NADH fluorescence signal is indicative of a stability of a contact between the distal tip of the ablation catheter and the tissue.

2. The method of claim 1 further comprising monitoring the amplitude of the NADH fluorescence signal during the delivering ablation energy to confirm that the distal tip remains in contact with the tissue.

3. The method of claim 1 further comprising stopping ablation of the tissue when the contact between the distal tip and the tissue is not stable.

4. The method of claim 1 further comprising collecting a spectrum of fluorescence light reflected from the illuminated tissue to distinguish tissue type.

5. The method of claim 1 wherein the tissue is illuminated with light having a wavelength between about 300 nm and about 400 nm.

6. The method of claim 2 wherein the step of monitoring comprises monitoring a level of the reflected light having a wavelength between about 450 nm and about 470 nm to identify peak NADH fluorescence.

7. The method of claim 1 wherein the catheter comprises a catheter body; the distal tip being positioned at a distal end of the catheter body for delivering ablation energy to the tissue, the distal tip defining an illumination cavity having one or more openings for exchange of light between the illumination cavity and tissue; and one or more optical fibers extending through the catheter body into the illumination cavity of the distal tip, the one or more optical fibers being in communication with a light source and a light measuring instrument to illuminate the tissue and to relay light energy reflected from the tissue to the light measuring instrument.

8. The method of claim 1 further comprising illuminating the tissue in a radial direction and an axial direction with respect to a longitudinal axis of the catheter.

9. The method of claim 1 further comprising providing a real time visual feedback about the lesion formation by displaying the level of NADH fluorescence.

10. The method of claim 1 wherein the ablation energy is applied when a NADH fluorescence peak is detected.

11. The method of claim 1 further comprising performing an ultrasound evaluation of the tissue in combination with monitoring the amplitude of the NADH fluorescence signal.

12. The method of claim 1, further comprising determining a normalized magnitude of the amplitude of the NADH fluorescence signal and displaying variations in a magnitude of the amplitude of the NADH fluorescence signal to the normalized magnitude of the amplitude of the NADH fluorescence signal.

13. The method of claim 12, wherein the variations in magnitude are used to determine stability of contact between the distal tip and the tissue.

14. The method of claim 2 wherein the step of monitoring comprises monitoring a level of the reflected light having a wavelength between about 375 nm and about 575 nm to identify peak NADH fluorescence.

15. A system for monitoring tissue ablation comprising:
a catheter comprising:
a catheter body; and
a distal tip positioned at a distal end of the catheter body, the distal tip having one or more openings for passing light energy to a tissue;
an ablation system in communication with the distal tip to deliver ablation energy to the distal tip;
a visualization system comprising a light source, a light measuring instrument, and one or more optical fibers in communication with the light source and the light measuring instrument and extending through the catheter body to the distal tip, wherein the one or more optical fibers are configured to pass light energy to the tissue;
a processor in communication with an ablation energy source, the light source and the light measuring instrument, the processor being programmed to:
receive NADH fluorescence data from the tissue illuminated with a light through the distal tip of the catheter during the delivery of ablation energy to the tissue; and
display an amplitude of an NADH fluorescence signal during the delivery of ablation energy, wherein the amplitude of the NADH fluorescence signal is indicative of a stability of a contact between the distal tip of the catheter and the tissue.

16. The method of claim 1 wherein the ablation energy is selected from the group consisting of radiofrequency (RF) energy, microwave energy, electrical energy, electromagnetic energy, cryoenergy, laser energy, ultrasound energy, acoustic energy, chemical energy, thermal energy, electroporation energy and combinations thereof.

17. The system of claim 15 wherein the processor is programmed to monitor the amplitude of the NADH fluorescence signal during the delivery of ablation energy to confirm that the distal tip remains in contact with the tissue.

18. The system of claim 15 wherein the tissue is illuminated with light having a wavelength between about 300 nm and about 400 nm.

19. The system of claim 15 wherein the processor monitors a level of a reflected light having a wavelength between about 450 nm and about 470 nm.

20. The system of claim 15 wherein the ablation energy is selected from the group consisting of radiofrequency (RF) energy, microwave energy, electrical energy, electromagnetic energy, cryoenergy, laser energy, ultrasound energy, acoustic energy, chemical energy, thermal energy, electroporation energy and combinations thereof.

21. The system of claim 15 wherein the catheter is configured to illuminate the tissue in a radial direction and an axial direction with respect to a longitudinal axis of the catheter.

22. The system of claim 15 wherein the catheter further comprises one or more ultrasound transducers and one or more electromagnetic location sensors and the system further comprises an ultrasound system in communication with the one or more ultrasound transducers for ultrasound evaluation of the tissue.

23. The system of claim 15 wherein the catheter further includes one or more electromagnetic location sensors and the system further includes a navigation system in communication with the one or more electromagnetic location sensors for locating and navigating the catheter.

24. The system of claim 15 wherein the processor is programmed to determine a normalized magnitude of the amplitude of the NADH fluorescence signal and to display variations in a magnitude of the amplitude of the NADH fluorescence signal to the normalized magnitude of the amplitude of the NADH fluorescence signal, wherein the variations in magnitude are used to determine stability of contact between the distal tip and the tissue.

25. A system for monitoring tissue ablation comprising:
an elongated body;
an ablation system associated with a distal tip of the elongated body for delivering ablation energy to a tissue;
a visualization system comprising a light source, a light measuring instrument, and one or more optical fibers in communication with the light source and the light measuring instrument and extending through the elongated body to the distal tip, wherein the one or more optical fibers are configured to pass light energy to the tissue to illuminate the tissue to excite NADH in the tissue;
a processor in communication with the visualization system, the processor being programmed to:
receive NADH fluorescence data from the tissue during the delivery of ablation energy to the tissue; and
display an amplitude of an NADH fluorescence signal during the delivery of ablation energy, wherein the amplitude of the NADH fluorescence signal is indicative of a stability of a contact between the distal tip of the elongated body and the tissue.

26. The system of claim 25 wherein the processor is programmed to monitor the amplitude of the NADH fluorescence signal during the delivery of ablation energy to confirm that the distal tip remains in contact with the tissue.

27. The system of claim 25 wherein the tissue is illuminated with light having a wavelength between about 300 nm and about 400 nm.

28. The system of claim 27 wherein the processor monitors a level of a reflected light having a wavelength between about 450 nm and about 470 nm.

29. The system of claim 27 wherein the processor monitors a level of a reflected light having a wavelength between about 375 nm and about 575 nm.

30. The system of claim 25 wherein the ablation energy is selected from the group consisting of radiofrequency (RF) energy, microwave energy, electrical energy, electromagnetic energy, cryoenergy, laser energy, ultrasound energy, acoustic energy, chemical energy, thermal energy, electroporation energy and combinations thereof.

31. The system of claim 25 wherein the processor is programmed to determine a normalized magnitude of the amplitude of the NADH fluorescence signal and to display variations in a magnitude of the amplitude of the NADH fluorescence signal to the normalized magnitude of the amplitude of the NADH fluorescence signal.

32. The system of claim 31, wherein the variations in magnitude are used to determine stability of contact between the distal tip and the tissue.

33. The system of claim 25 further comprising a balloon disposed at the distal tip of the elongated body.

* * * * *